United States Patent [19]
Perry

[11] 4,449,975
[45] May 22, 1984

[54] INTRAVENOUS ANCHOR AND WOUND SHIELD

[76] Inventor: Michael K. Perry, 3711 NE. Winn Rd., Kansas City, Mo. 64117

[21] Appl. No.: 319,693

[22] Filed: Nov. 9, 1981

[51] Int. Cl.³ .............................................. A61M 25/02
[52] U.S. Cl. ................................... 604/179; 128/133; 128/DIG. 26; 604/180
[58] Field of Search ................... 128/133, 214 R, 215, 128/348–350 R, DIG. 26; 604/174–180

[56] References Cited

U.S. PATENT DOCUMENTS

| | | | |
|---|---|---|---|
| 3,059,645 | 10/1962 | Hasbrouck et al. | 128/133 |
| 3,812,851 | 5/1974 | Rodriguez | 128/133 |
| 3,834,380 | 10/1974 | Boyd | 128/133 |
| 4,250,880 | 2/1981 | Gordon | 128/214 R |
| 4,316,461 | 2/1982 | Marais et al. | 128/214 R |

Primary Examiner—Dalton L. Truluck
Attorney, Agent, or Firm—Hiram A. Sturges

[57] ABSTRACT

An intravenous catheter and anchoring set comprising a catheter assembly having an I.V. catheter having one end inserted into the limb of a patient and a flexible tube attached to the other end of the catheter, a flexible anchor base, the base having notches therein forming adjustable bands extendible around a limb, attachment means attaching the bands together and skin-anchor adhesive means on the inner side of the base and capable of holding the base to the skin while the bands are being adjustably secured in place.

8 Claims, 4 Drawing Figures

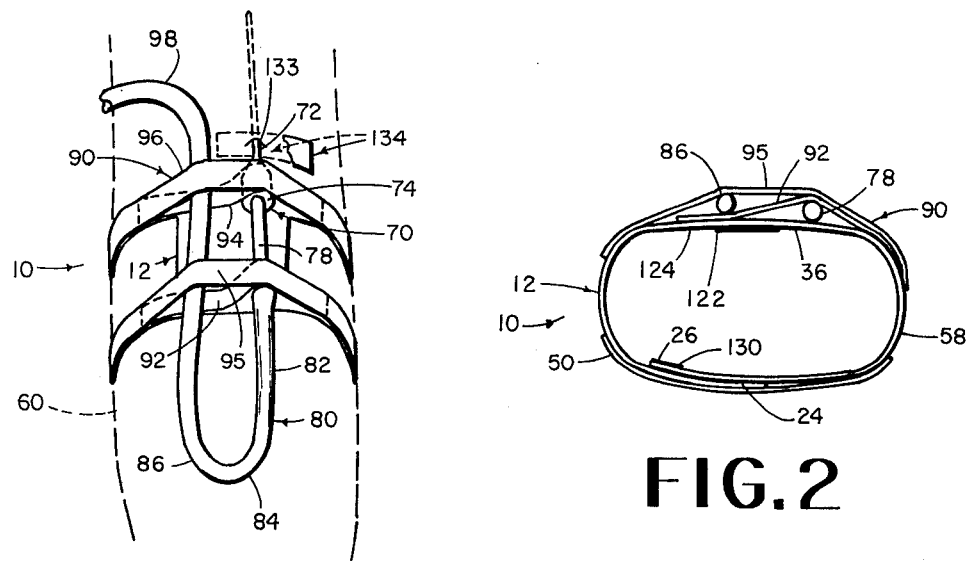
FIG.1
FIG.2
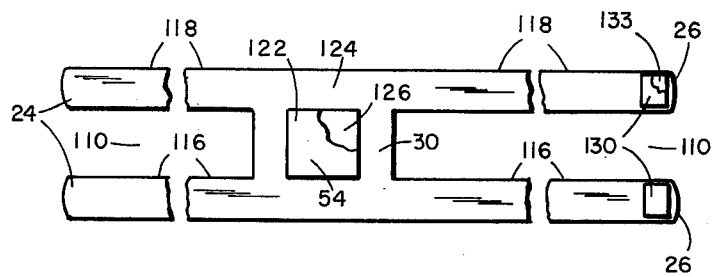
FIG.3
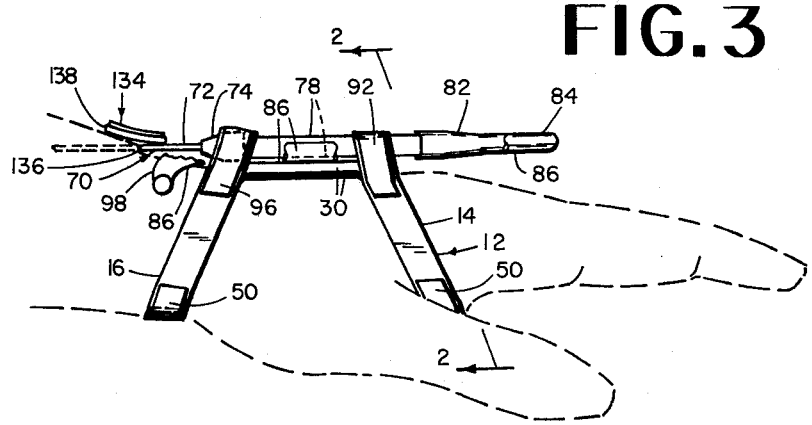
FIG.4

INTRAVENOUS ANCHOR AND WOUND SHIELD

BACKGROUND OF THE INVENTION

In the prior art great pain and stress has been experienced by weakened patients as catheter anchoring tape is removed from the skin.

It is, therefore, an object of this invention to provide an anchor base, preferably made of flexible plastic which can be wrapped around the wrist or all taping can be done on the top of the anchor base and the anchor base itself acts as a substitute for the patient's skin, whereby the patient's skin is not painfully distressed as it would be in the prior art method when the tape is removed.

In the new way hereof, the removing of tape is from the anchor base itself. In this way the anchor base acts as a "substitute skin."

In the prior art catheter stabilizers have been proposed in which the intention is to anchor the stabilizer without any bands extending around the wrist. Such a way is shown in U.S. Pat. No. 4,250,880, issued Feb. 17, 1981, to Marvin Gordon, entitled STABILIZING FITTING FOR AN INTRAVENOUS CATHETER.

It is an object of this invention to provide an anchoring system in which the amount of adhesive contact with the skin is much lesser for the reason that the adhesive material under the base of the anchor can be a very small area since it does not need to assist adhesive tape in holding the catheter in place. Having the adhesive material which is secured to the base of very small size reduces the discomfort when the base is removed from the patient's skin, whereby not as many skin areas are pulled loose painfully. Likewise the absence of adhesive tape in contact with the skin to hold the base reduces the pain that would result from the removal of the tape.

In addition, the firmness of anchoring is believed to be more secure when bands go completely around the arm.

Another objective is to provide an anchor which has a minimal die cost for low cost manufacturing.

A U.S. Pat. No. 4,316,461, issued Feb. 23, 1982 to Henri J. Marais and titled INTRAVENOUS VASCULAR STABILIZER shows two bands attached to a base. The adhesive area under the base covers the entirety of a large base which would make painful removal from a patient's arm when adhesive coating must be pulled away from the skin hair, etc. This painful removal would be especially large because of the great area of the adhesive coating.

It is, therefore, an object of this invention to provide a base making use of my discovery that a very small adhesive coating is all that is needed for temporary positioning where bands are being tightened.

Bands that have stages in their final positions because of the use of spaced apertures to receive protruding buttons do not provide for the tightening of bands to positions between the apertures, whereby the choice is for the band to be somewhat more loose than ideal, or somewhat more tight than ideal. It is, therefore, an object of this invention to provide a method of holding the bands in place which allows for their positioning at any degree of tightness, rather than only at a selected spaced stage of tightening.

Speed of application can be very important in emergency times. It has been discovered that the use of very small adhesive areas at one end of each of two bands is of great assistance in holding both ends in place when the other ends of the same bands are brought around to positions for connection thereto.

The use of small adhesive portions at the ends of bands and at the same time using a small adhesive portion under the base makes a combination of advantage because then none of these adhesive portions need be of any considerable size, whereby pain is reduced during removal. Portions under the bands enhance stability and cooperation with the portion under the base so that it all can be of small area to the comfort of the patient.

An important objective is to provide skin-anchor adhesive for attaching the underside of the base to a limb to hold the base in place while its bands are being secured in place.

BRIEF DESCRIPTION OF THE DRAWINGS

FIG. 1 is a perspective view of the intravenous catheter and placement set of this invention comprising an anchoring set and catheter shown in full lines, except for hidden parts, which latter are shown in dotted lines, and a wound shield adhesive bandage, which latter is shown partially in full lines and the remainder is broken away and shown in dotted lines. This view shows the placement set on a patient's forearm, which latter is partially shown in dotted lines.

FIG. 2 is a sectional view taken along the line 2—2 of FIG. 4, but purposely does not show the rearward three-fourths of the catheter and placement set.

FIG. 3 is a bottom plan view of the anchorbase portion of the placement set and is shown with portions broken away and with skin anchor adhesive thereon in a central position and also on ends thereof. Protective coverings for two of the adhesive skin anchors are shown only partially and the remainder broken away to show adhesive thereunder.

FIG. 4 is a side elevation of the intravenous catheter and anchoring and placement set of this invention shown in place on a patient's hand and wrist, which latter are shown in dotted lines, a closer half portion of the adhesive bandage wound shield being broken away and the remainder shown in section, only a forward section, a rearward section and a part of a central section of a third portion of flexible tubing being shown and two sections of the third portion being broken away for showing parts therebehind.

DESCRIPTION OF THE PREFERRED EMBODIMENT

The intravenous catheter and anchoring set of this invention is generally indicated at 10 in FIG. 1 and comprises a substantially flexible anchor base generally indicated at 12 having forward and rearward sides 14 and 16, as best seen in FIG. 4, and having right and left end portions 24 and 26, as best seen in FIGS. 2 and 3.

The terms "right" and "left", as used as regards the end portions are in the position of the anchoring set as its central portion 30 is rested across the top of a patient's wrist before the end portions are wrapped around the wrist. For this reason, in FIG. 2, the end portion 24 is on the left side, as shown, because it wraps far enough to overlap to the left side of the wrist and the left end portion 26 has come to be on the right side of the patient's wrist because of its having been wrapped around under the wrist.

The base 12 is elongated from right to left and has a wide first side 36 that forms the inner side of the base 12 when the base is wrapped around the patient's arm and is in the shape shown in FIG. 2.

The base 12 has a length for extending at least the majority of the length around the patient's arm and preferably completely around a patient's arm, and still more preferably a length sufficient to extend around a patient's arm and overlap itself, as shown in FIG. 2. Such length can vary with different patients, and whether they are adult patients or children, and also still longer bases can be used going around larger limbs, such as parts of adult legs, etc.

Suitable end connectors shown at 50 are used for connecting right and left portions of the base together after they have been wrapped around the wrist. A preferred form of the connector 50 is simply a length of adhesive tape engaging the outer side of each half portion of the base. To illustrate, the base can be regarded as having a center at the numeral 54 in FIG. 3 in the center of the central portion 30 of the base, whereby all other parts of the base are then to the right or left of the center so that after the base is wrapped around a patient's limb, such as the arm 60 of the patient shown in FIG. 1, then the ends 24 and 26 will be overlapped and the right and left half portions of the base will have an outer side 58, shown in FIG. 2, and it across the outer side 58 of the right and left half portions of the base that the connector tape 50 is caused to extend and adhere to for binding together the right and left half portions of the base on the underside of the patient's arm 60.

A catheter assembly is generally indicated at 70 in FIG. 1 and has a hollow I.V. or intravenous catheter 72.

The catheter assembly 70 also includes a hub which is of a larger diameter than the catheter insertable tube portion 72. The catheter assembly 70 includes a stiff outer tube 78 of larger diameter than the insertable tube 72 and of lesser diameter than the hub 74. Thus a standard catheter is described.

It is also common for a flexible tube, such as a rubber tube 80, to be attached to the outer end of the tube 78 and the tube 80 has a first portion 82 attached to and extending away from the outer tube 78 and extending forwardly therefrom across the base 12 and having a second portion 84 attached to the first portion 82 and which is curved to make a connection with the third portion 86 of the tube 80, which latter extends rearwardly alongside of the first portion 82 and in substantial paralellism therewith.

The catheter assembly 70 is secured to the base 12 preferably by means of securing assembly generally indicated at 90 and comprising a first and inner piece of adhesive tape 92 which extends lengthwise of the base 12 and transversely of the patient's arm 60 and transversely of the stiff tubing section 78 so as to extend across the tubing section 78 and adhesively secured to the base 12 on each side of the section 78.

The securing assembly 90 further includes a rearward or second adhesive piece 94, which latter is seen in FIG. 1 and is not shown in FIG. 2 because FIG. 2 purposely does not show the rearward half of the anchoring set 10. The second piece 92 extends from a side of the base 12 up and over the hub 74 of the catheter assembly 70, preferably extending across that portion of the hub 74 which tapers inwardly to the diameter of the insertable portion 72 of the catheter assembly 70, although the remainder of the tape piece 94 extends across the larger diametered portion of the hub 74.

The securing assembly 90 further includes forward and rearward outer tape pieces which can be called third and fourth adhesive tape pieces 95 and 96, which latter extend across the top of the respective first and second pieces 92 and 94, but extend across the top also of the third tubing section 86 and downwardly on the opposite side of the base 12 so as preferably to be engaged directly with the base 12 on both the left and right sides of the base 12.

As thus described, any force that would pull on the tubing 80 and a fourth section 98 thereof which is connected to the third section 86 would not pull against the catheter 70 at all, but would only pull against the tape pieces 95 and 96 and against the firmly mounted base 12.

The base 12, as best seen in FIG. 3, has right and left notches 110 extending inwardly from each of its ends up to its central portion 30, whereby forward and rearward bands 116 and 118 are defined, which latter extend from right to left the length of the base and are joined together by central portion 30.

It is around these bands 116 and 118 that the adhesive tape pieces 50 are placed.

The notches 110 together total a lengthwise dimension as measured lengthwise of the base 12, or from right to left, a distance which is at least the majority of the length of the base.

The entire anchoring set 10, including the base 12 and the tapes 50 and the tapes 92, 94, 95 and 96, are all sufficiently transparent as to substantially provide visibility therethrough sufficient for a person to substantially see inflammation of a patient's skin in a central area of the base extending one-half inch forwardly of the rearward end of the base adjacent the narrow portion 72 of the catheter assembly and one inch from right to left under the first portion 82 of the tubing 80.

A first or central skin anchor adhesive element or coating 122 is secured to the inner side 124 of the base 12 and is covered by a protective cover 126, partially shown in FIG. 3, and which can be peeled off in a conventional manner.

Second and third skin anchor adhesive elements or coatings called end anchoring elements 130, as seen in FIG. 3, can be secured to each of the ends of the bands 116 and 118 at one end of the base 12 and are preferably covered by removable coverings 133, a portion of one of which is shown at 133 in FIG. 3.

The anchor base 12 has a length for extending around a patient's arm, and in other uses a length for extending around a patient's leg. For an adult female this may require four inches of length plus extra length for overlap, siuch as two extra inches for overlap if the adult is small, whereby a total of six inches would be needed. For the same result in a larger female adult, eight inches would be necessary, including one inch overlap. These dimensions are for going around a wrist, and larger dimensions are needed to go around a hand between the first and index fingers. Still larger dimensions are needed to go around a leg. Smaller dimensions are adequate for children, especially infants.

In the sequence of installation, first the catheter is inserted into the patient's limb, and the wound 133 is covered with an antiseptic 136. Then the area of the wound is covered by an adhesive bandage 134, called the wound shield herein. The bandage 134 has a pad 138 of porous nature on its underside, and it is to this pad that adhesive can be applied in the process of putting the adhesive on the wound area, if desired, simultaneously with the shield 134. Only a very small adhesive bandage of perhaps one inch in length is sufficient because the wound is very small. Although this is in contrast with the two-inch by two-inch pads used in the prior art and not shown herein.

Next, the base 12 is placed under the outer end of the catheter 70, although first the covering 126 is removed from the first or central skin anchoring adhesive 122, so that the central skin anchoring element 122 can be pressed against the skin for adhering thereto by pressing on the opposite side of the base 12. This holds the anchor base 12 in place on the limb 60 so that the ends of the bands 116 and 118 can be more easily put in place.

While wrapping the bands 116 and 118 around the limb 60, the end skin anchoring elements 130 are first pressed against the skin to hold one end of each band 116 and 118 in place, while the other end has one of two lower pieces of adhesive tape 50 attached thereto.

Next, sequentially, each piece of tape 92 and 94 is put in place so the anchor base 50 is quickly and firmly held to the patient with minimum adhesive engagement with the patient's skin so as to reduce pain during removal. By this means the amount of adhesive which engages the skin is at a minimum for greater comfort and lesser pain.

The bands 116 and 118 are preferably each of three-fourths inch thickness, slightly larger than the one-half inch adhesive tape common to hospitals for ease of placement of tape thereon. The central adhesive element 122 is one-half inch square and the end elements 130 are smaller yet for a minimumof adhesive-skin contact. The central section 30 of the base can be about two and one-eighths inches from a notch 110 to the other notch 110.

The notches 110 provide the band portions 116 and 118 with free ends so one can go around the hand between thumb and first finger. This gives good anchoring in a difficult area. The bands 116 and 118 are preferably nine-sixteenths inch apart fro a base to be of a minimum skin covering and bulk consistent with good anchoring, about two and one-sixteenth inches wide.

I claim:

1. An intravenous catheter and anchoring set comprising:

a substantially flexible anchor-base having forward and rearward sides and right and left end portions, said base being elongated from right to left, said base having a first side that can form the inner skin-facing side of said base when said base is wrapped around a patient's arm, end-connecting means connecting said right and left end portions of said base together, and a catheter assembly, said catheter assembly having a hollow I.V. catheter having one end insertible into a patient's limb, a flexible tube attached to the other end of said catheter, and means securing said catheter assembly to said base, a skin anchor means of skin-gripping adhesive material secured to said base on and facing away from said inner skin-facing first side thereof and capable of adhering to the skin of a patient sufficiently to assist the attachment of said base to the arm of a patient by holding said base in place, said base having a notch means formed in at least one end thereof and providing forward and rearward bands and an interconnecting portion extending transversly to and between said band connecting said bands, the length of said base, each of said bands having a right end and a left end, said bands each having a length and flexibility for freely wrapping substantially completely about a patient's arm, means releasably attaching the ends of at least one of said bands together in an adjustable manner accomplishing variations in size of the space enclosed by said one band and defining said end-connecting means.

2. The intravenous catheter and anchoring set of claim 1 and having said skin anchor means having a portion secured to a central part of said base.

3. The intervenous catheter and anchoring set of claim 1 having said notche means together totalling in lengthwise dimension of said base a distance which is at least the majority of the length of said base.

4. The intravenous catheter of claim 1 having said skin anchor means being on an end part of one of said bands and being of a much lesser size than the underside of said interconnecting portion of said base.

5. The intravenous catheter of claim 4 having said s kin anchoring means being at least partly on a central part of said base, said skin anchor means portion which is on a central part of said base being of smaller size than said interconnecting portion for lesser pain during removal of the anchoring set from a patient.

6. The intravenous catheter of claim 1 having said skin anchor means having a portion secured to an end part of one of said bands.

7. The intravenous catheter and anchoring set of claim 1, said end connecting means comprising adhesive tape means.

8. The intravenous catheter of claim 1 having said end portion of said skin anchor means of approximately the area of a square having sides of one-half inch size.

* * * * *